United States Patent
Longoria et al.

(10) Patent No.: US 10,786,297 B2
(45) Date of Patent: Sep. 29, 2020

(54) METHODS OF PERFORMING CARDIAC SURGICAL PROCEDURES AND KITS FOR PRACTICING THE SAME

(71) Applicant: Charles Somers Living Trust, McClellan, CA (US)

(72) Inventors: James Longoria, Sacramento, CA (US); Roy Chin, Pleasanton, CA (US)

(73) Assignee: Charles Somers Living Trust, McClellan, CA (US)

( * ) Notice: Subject to any disclaimer, the term of this patent is extended or adjusted under 35 U.S.C. 154(b) by 0 days.

(21) Appl. No.: 14/297,062

(22) Filed: Jun. 5, 2014

(65) Prior Publication Data
US 2014/0371741 A1   Dec. 18, 2014

Related U.S. Application Data

(60) Provisional application No. 61/835,266, filed on Jun. 14, 2013.

(51) Int. Cl.
| | | |
|---|---|---|
| *A61B 18/14* | (2006.01) | |
| *A61B 17/12* | (2006.01) | |
| *A61B 18/00* | (2006.01) | |
| *A61B 18/20* | (2006.01) | |
| *A61B 18/02* | (2006.01) | |
| *A61N 7/02* | (2006.01) | |
| *A61B 18/18* | (2006.01) | |
| *A61B 17/072* | (2006.01) | |
| *A61B 17/00* | (2006.01) | |

(52) U.S. Cl.
CPC ........ *A61B 18/14* (2013.01); *A61B 17/12122* (2013.01); *A61B 17/12181* (2013.01); *A61B 17/07207* (2013.01); *A61B 17/12009* (2013.01); *A61B 17/12109* (2013.01); *A61B 18/02* (2013.01); *A61B 18/1442* (2013.01); *A61B 18/18* (2013.01); *A61B 18/20* (2013.01); *A61B 2017/00243* (2013.01); *A61B 2018/00005* (2013.01); *A61B 2018/0016* (2013.01); *A61B 2018/00345* (2013.01); *A61B 2018/00351* (2013.01); *A61B 2018/00357* (2013.01); *A61B 2018/00369* (2013.01); *A61B 2018/00375* (2013.01); *A61B 2018/00416* (2013.01); *A61B 2018/1467* (2013.01); *A61N 7/02* (2013.01)

(58) Field of Classification Search
CPC ..... A61B 18/02; A61B 18/12; A61B 18/1266; A61B 18/14; A61B 18/1442; A61B 18/1445; A61B 18/1448; A61B 18/18; A61B 18/20; A61B 2018/00345; A61B 2018/00351; A61B 2018/00357; A61B 2018/00369; A61B 2018/00375; A61B 2018/00416; A61B 2018/1467; A61N 7/02

USPC ...................................................... 606/41–50
See application file for complete search history.

(56) References Cited

U.S. PATENT DOCUMENTS

| | | | |
|---|---|---|---|
| 2002/0087151 A1* | 7/2002 | Mody | A61B 18/1492 606/15 |
| 2003/0120268 A1 | 6/2003 | Bertolero et al. | |
| 2005/0224086 A1* | 10/2005 | Nahon | A61B 18/02 128/899 |
| 2006/0084969 A1* | 4/2006 | Truckai | A61B 18/1482 606/41 |
| 2006/0089637 A1* | 4/2006 | Werneth | A61B 18/1492 606/41 |
| 2008/0033457 A1 | 2/2008 | Francischelli et al. | |
| 2008/0097297 A1* | 4/2008 | Kelley | A61B 18/1477 604/103.01 |
| 2010/0185186 A1* | 7/2010 | Longoria | A61B 18/02 606/2 |

OTHER PUBLICATIONS

Burgess et al., "Interventions for Prevention of Post-Operative Atrial Fibrillation and its Complications after Cardiac Surgery: a Meta-Analysis", European Heart Journal (2006), 27:2846-2857.
Crystal et al., "Interventions on Prevention of Postoperative Atrial Fibrillation in Patients Undergoing Heart Surgery: a meta-analysis", Journal of the American Heart Association Circulation (2002), 106(1):75-80.
Davis et al., "Strategies for the Prevention of Postoperative Atrial Fibrillation in Cardiac Surgery", Special Topics in Cardiac Surgery, Chapter 9, Published in Feb. 29, 2012.
Enchahidi et al., "Mechanisms, Prevention, and Treatment of Atrial Fibrillation After Cardiac Surgery", J Am Coll Cardiol (2008), 51(8):793-801.
Maesen et al., "Post-operative atrial fibrillation: a maze of mechanisms", Europace (2011) doi: 10.1093/europace/eur208, First published online: Aug. 6, 2011.
Melo et al., "Ventral cardiac denervation reduces the incidence of atrial fibrillation after coronary artery bypass grafting", J Thorac Cardiovasc Surg (2004), 127(2):511-516.
Omae et al., "Management of postoperative atrial fibrillation", J Anesth (2012), 26(3): 429-437.
Salazar et al., "Stroke After Cardiac Surgery: Short- and Long-Term Outcomes", Ann Thorac Surg (2001), 72(4):1195-1201.

(Continued)

*Primary Examiner* — Michael F Peffley
*Assistant Examiner* — Khadijeh A Vahdat
(74) *Attorney, Agent, or Firm* — Heisler & Associates

(57) ABSTRACT

Aspects of the present disclosure include methods of performing a cardiac surgical procedure on a subject. The methods include performing the cardiac surgical procedure in combination with pulmonary vein isolation and left atrial appendage modification. Kits for use in performing a cardiac surgical procedure are also provided, the kits including a device configured to perform a pulmonary vein isolation procedure, and a device configured to perform a left atrial appendage modification.

8 Claims, No Drawings

(56) References Cited

OTHER PUBLICATIONS

Saltman, "New-onset postoperative atrial fibrillation: a riddle wrapped in a mystery inside an enigma", J Thorac Cardiovasc Surg (2004), 127(2):311-313.
Vohra et al., "Surgery for Atrial Fibrillation", Special Topics in Cardiac Surgery, Chapter 11, Published in Feb. 29, 2012.
Wilber, Transseptal versus retrograde approach in "Catheter Ablation of Cardiac Arrhythmias: Basic Concepts and Clinical Applicaitons", Sep. 22, 2011, John Wiley & Sons, XP055326135, *Retrogarde Approach*.
Wolf et al., Video-assisted bilateral pulmonary vein isolation and left atrial appendage exclusion for atrial fibrillation, J Thorac Cardiovasc Surg. Sep. 2005:130(3):797-802.

* cited by examiner

METHODS OF PERFORMING CARDIAC SURGICAL PROCEDURES AND KITS FOR PRACTICING THE SAME

CROSS-REFERENCE TO RELATED APPLICATIONS

Pursuant to 35 U.S.C. § 119 (e), this application claims priority to the filing date of U.S. Provisional Patent Application Ser. No. 61/835,266 filed Jun. 14, 2013; the disclosure of which application is herein incorporated by reference.

INTRODUCTION

Atrial fibrillation (AF) occurs in 15% to 50% of patients after cardiac surgery and represents the most common postoperative arrhythmic complication. Postoperative atrial fibrillation (POAF) most often develops between the second and fifth postoperative day, with a peak incidence in the first two to three days. While POAF can be self-limiting, it may also be associated with hemodynamic compromise, postoperative stroke, perioperative myocardial infarction (MI), ventricular arrhythmias, and heart failure. The development of POAF is associated with an additional hospital length of stay (LOS) of 1 to 1.5 days on average, and up to 5 days in some instances.

Practice guidelines for the prevention of POAF in patients undergoing cardiac surgery exist. The guidelines consistently recommend using beta-blockers to reduce the incidence of POAF, with sotalol and amiodarone being effective alternatives depending upon the contraindication. Some guidelines include consideration of corticosteroids for the prevention of POAF. Also recommended by certain practice guidelines is the utilization of non-pharmacologic strategies for the prevention of POAF in cardiac surgery patients, the primary strategy being cardiac pacing (e.g., biatrial pacing).

Stroke remains one of the most prominent potential complications of cardiac surgery. The incidence of stroke in this population has been estimated from 1.6% to 5.2%. Of the more than 400,000 adult patients in the United States and 800,000 patients worldwide who undergo cardiopulmonary bypass procedures each year, up to 21,000 patients nationally and 42,000 patients worldwide will suffer stroke. The economic impact of stroke after coronary revascularization is estimated to exceed $2 to $4 billion annually worldwide.

SUMMARY

Aspects of the present disclosure include methods of performing a cardiac surgical procedure on a subject. The methods include performing the cardiac surgical procedure in combination with pulmonary vein isolation and left atrial appendage modification, whether or not the patient has atrial fibrillation during a cardiac procedure. Kits for use in performing a cardiac surgical procedure are also provided, the kits including a device configured to perform a pulmonary vein isolation procedure, and a device configured to perform a left atrial appendage modification.

DETAILED DESCRIPTION

Aspects of the present disclosure include methods of performing a cardiac surgical procedure on a subject. The methods include performing the cardiac surgical procedure in combination with pulmonary vein isolation and left atrial appendage modification. Kits for use in performing a cardiac surgical procedure are also provided, the kits including a device configured to perform a pulmonary vein isolation procedure, and a device configured to perform a left atrial appendage modification.

Before the methods of the present disclosure are described in greater detail, it is to be understood that the methods of the present disclosure are not limited to particular embodiments described, as such may, of course, vary. It is also to be understood that the terminology used herein is for the purpose of describing particular embodiments only, and is not intended to be limiting, since the scope of the methods of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Methods

As summarized above, the present disclosure provides methods of performing a cardiac surgical procedure on a subject. The methods include performing the cardiac surgical procedure in combination with pulmonary vein isolation and left atrial appendage modification.

As used herein, the term "cardiac surgical procedure" broadly refers to a surgical procedure performed on any tissue of the heart (e.g., cardiac muscle tissue, nerve tissue, vascular tissue and/or the like) and/or a surgical procedure for treatment of a heart condition, e.g., a condition caused by a blockage or restriction in the blood flow leading to the heart or from the heart. Cardiac surgical procedures of interest include, but are not limited to, open heart surgical procedures, heart valve procedures, procedures that include opening the pericardium (e.g., where the pericardium is opened via a protocol selected from thoracoscopy, thoracotomy, mediastinotomy, sternotomy, subxiphoid, and trans-diaphragmatic route), bypass procedures (e.g., coronary artery bypass grafting procedures), arrhythmia treatment procedures, aneurysm repair procedures, and any combination thereof. In certain aspects, the cardiac surgical procedure includes two or more of: a coronary artery bypass grafting procedure, an arrhythmia treatment procedure, and an aneurysm repair procedure.

The cardiac surgical procedure, pulmonary vein isolation and left atrial appendage modification is performed on a subject. The term "subject" is used interchangeably herein with the term "patient". In certain embodiments, a subject is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" may include human subjects of both genders and at any stage of development (e.g., fetal, neonates, infant, juvenile, adolescent, and adult), where in certain embodiments the human subject is a juvenile, adolescent or adult. While the methods described herein may be applied to perform a cardiac surgical procedure on a human subject, it is to be understood that the subject methods may also be carried out to perform a cardiac surgical procedure on other subjects (that is, on "non-human subjects").

According to certain embodiments, the method is performed regardless of whether the subject—prior to the cardiac surgical procedure—has atrial fibrillation or has been diagnosed as having a predisposition to atrial fibrillation, e.g., a predisposition to experience postoperative atrial fibrillation. For example, in certain aspects, the method is performed on a subject who has not been diagnosed as having a predisposition to experience post-operative atrial fibrillation. The absence of the subject being diagnosed as having a predisposition to experience postoperative atrial fibrillation may be on the basis that tests for diagnosing such a predisposition were not performed on the subject, or diagnostics tests were performed and the subject did not exhibit the requisite clinical features to diagnose the subject as having a predisposition to experience postoperative atrial fibrillation.

In certain aspects, the method is performed on a subject who has been diagnosed as having a predisposition to post-operative atrial fibrillation. Example approaches for diagnosing a predisposition to post-operative atrial fibrillation include, but are not limited to, physical examination, electrocardiogram (EKG; ECG); a Holter monitor, which is an EKG recorded over a 24-hour period to detect arrhythmias that may happen briefly and unpredictably throughout the day, imaging studies such as chest x-ray, ultrasound, computerized tomography (CT), magnetic resonance imaging (MRI), nuclear medicine studies such as a nuclear myocardial stress test, for example. Additionally, invasive studies including cardiac catheterization with electrophysiologic studies may be performed.

Methods of the present disclosure include performing the cardiac surgical procedure in combination with pulmonary vein isolation. The pulmonary veins return oxygenated blood from the lungs to the left atrium. There are typically four pulmonary veins, a superior pulmonary vein and an inferior pulmonary vein from each lung. On the right side of the heart, the superior pulmonary vein passes posterior to the superior vena cava, the inferior behind the right atrium. On the left side of the heart, both the superior and inferior pulmonary veins pass anterior to the descending thoracic aorta.

By "pulmonary vein isolation" is meant a partial or complete electrical isolation of one, two, three, or four pulmonary veins from the left atrium of the heart. Electrical isolation may be achieved using an ablative device (e.g., an ablative surgical device) to ablate a target tissue of interest. By "ablative" or "ablate" is meant the removal or alteration of electrically-conducting tissue in a target area of interest (e.g., a circumferential ablation region surrounding a pulmonary vein ostium, or two or more (e.g., each) of the four pulmonary vein ostia), such that the tissue no longer conducts or generates an electrical impulse sufficient to generate or propagate an arrhythmia. The process of ablation can prevent an arrhythmia from developing because the tissue that provides a trigger for an arrhythmia has been destroyed. The process of ablation can also prevent an arrhythmia from propagating to other areas of the heart by the creation of a line, or lesion, which electrically isolates the tissue and blocks passage of the electrical impulse. Ablation can be performed with a variety of types of energy, such as radiofrequency energy, laser energy, microwave energy, cryothermy, and the like. Ablation "lines" or "lesions" can be focal areas which are separate from other areas of ablation, or they can be contiguous, such they form lines or lesions connected to each other, which can form, for example, a continuous line, or ring, or circle, in order to electrically isolate the pulmonary vein(s).

In some embodiments, ablation can be performed by directly contacting a portion of cardiac tissue with an ablative device in a manner sufficient to create a lesion. In other embodiments, ablation can be performed by delivery of an ablating agent to cardiac tissue. For example, in some embodiments, an ablation device can be located sufficiently close to an area of cardiac tissue of interest, such that an ablating agent, (e.g., radiofrequency or laser energy) is delivered to the cardiac tissue in a manner sufficient to create a lesion. The form of energy used for ablating cardiac tissue can be radiofrequency, laser or cryoablation energy, for example. In some embodiments, the ablation is transmural, i.e., extends through the entire heart wall. In other embodiments, the ablation does not extend through the entire thickness of the cardiac wall; however, the degree of ablation may be sufficient to block electrical conduction.

The ablative device may be contacted with a portion of cardiac tissue to form a lesion. The methods can further include repeating the contacting and ablating a number of times to produce a plurality of lesions. For example, the contacting step may be performed two or more times, such as three or more, or four or more times, etc. In some embodiments, the contacting and ablating step is performed in the same location. In some embodiments, the contacting and ablating step can be performed in overlapping locations, such that part of a second location overlaps with part of a first ablating location, such as in the case of creating a continuous linear ablation line. In other embodiments, a second ablation step may be in a different location from the first ablation step, e.g. to create circumferential lesions around the connection area between a pulmonary vein and the left atrium.

As summarized above, the pulmonary vein isolation may be performed using an ablative surgical device. An ablative surgical device of the subject methods can be in the shape of a clamp, with an upper and a lower jaw, such that the ablation device is a clamping device. In other embodiments, the ablative device can have an elongated cylindrical shape, such as that of a pen. In some embodiments, the ablation device can have a linear shape, a rectangular shape, a semi-circular shape, an "L" shape, a "U" shape, or any other suitable shape. The configuration of the surface of the ablation device that contacts the tissue can also be any suitable two-dimensional shape such as a line, a square, an oval, a triangle, etc. In some embodiments, the ablation device can further employ suction to pull tissue into the device.

In certain aspects, the ablative surgical device is a radiofrequency (RF) ablative surgical device. Such devices deliver radiofrequency energy to a target tissue of interest. The heat generated by the RF energy ablates the tissue, resulting in the formation of scar tissue at the ablation site. In certain aspects, the radiofrequency ablative surgical device is a single point radiofrequency ablative surgical device, e.g., a device that transmits RF energy from a single point at the tip of the device. Single point radiofrequency ablative surgical devices typically ablate a "spot" of tissue, such that isolating the pulmonary vein may entail ablating one spot after another to make a circumferential line surrounding a pulmonary vein ostium, similar to drawing a line by making a series of contiguous dots. In other aspects, the radiofrequency ablative surgical device is a multielectrode (e.g., "multipolar") radiofrequency ablative surgical device, e.g., a device which transmits RF energy from two or more electrodes (e.g., 2, 3, 4, 5, 6, 7, 8, or more electrodes). When the subject methods employ a multielectrode radiofrequency ablative surgical device, the device may be a bipolar or quadripolar ablative surgical device. The terms "bipolar" and "quadripolar" indicate that the ablation path extends locally between two or four electrodes (respectively) in the device, rather than between one electrode and a general remote, or external electrode. Such devices may be configured to deliver ablation energy to achieve a uniform, superficial depth of ablation between ~500 µm and ~1,000 µm.

In some instances, RF tissue ablation devices are employed that include an elongated member having a proximal and distal end, first and second jaws at the distal end, wherein the first and second jaws are configured to apply intra and inter RF energy to tissue disposed between the jaws during use, and a connector at the proximal end for operatively connecting to a RF energy source. In some instances, at least one of the first and second jaws comprises two or more elongated electrodes. The elongate electrodes may span the length of the tissue contact area of each jaw, or just a portion thereof. In some instances, the length of the active area elongated electrodes ranges from 0.5 to 5 cm, such as 0.75 to 4 cm and including 1 to 2.5 cm. The width of the active area of each electrode may also vary, and in some instances ranges from 0.1 to 2.5 cm, such as 0.25 to 1 cm and including 0.25 to 0.75 cm. In some instances, each of the first and second jaws comprises two or more elongated electrodes, such as three, four or five or more elongated electrodes. The number of elongated electrodes on each of the first and second jaws may be the same or different. The configuration of each elongated electrode may also vary, and therefore may be linear, curvilinear, angled, etc., as desired. Each of the elongated electrodes of the first and second jaws may be made up of any convenient material. Electrode materials of interest include, but are not limited to: platinum group metals, such as platinum, rhodium, palladium, rhenium, as well as tungsten, gold, silver, tantalum, and alloys of these metals; electrically conductive elastic materials, such as nickel/titanium alloys, copper/zinc alloys, or nickel/aluminum alloys; etc. In some instances, the elongated electrodes include a positive temperature co-efficient of resistivity (PTCR) material, e.g., where the PCTR material may be present as a coating on the active surface of the electrode, or otherwise incorporated into the electrode. PTCR materials of interest include semiconductor materials which exhibit resistivity increases with increasing temperature, specifically an increase that is characterized by a slow increase in resistivity up to a the Curie temperature of the material. When a PTCR material reaches its Curie temperature, its resistivity increases by several orders of magnitude over a very small temperature range. Thus, the amount of current that can flow is very small compared to that which can flow at significantly lower temperatures. After this sharp rise, the resistivity approaches an almost constant value. As such, PTCR materials of interest are those that first undergo a slow increase in resistance as the temperature increases. In the region of their characteristic Curie temperature, their resistivity increases dramatically over a very small temperature range. After this rapid increase, the resistivity approaches a maximum as the temperature rises further. PTCR materials of interest include those having a Curie temperature ranging from 60 to 160 ° C., such as 75 to 150 ° C. and including 80 to 125° C. Materials exhibiting PTCR properties include, but are not limited to: semiconducting titanate ceramics, such as but not limited to barium titanate, lead titanate and strontium titanate; ternary perovskites, e.g., $BaTiO_3$, and the like; etc., where these materials may include small amounts of dopants sufficient to provide for the desired semi-conductive property, where dopants of interest include, but are not limited to: trivalent ions (e.g., $Y^{3+}$, $La^{3+}$, $Nd^{3+}$, $Sm^{3+}$, etc.) and the like. Also of interest as PTCR materials are PTC matrix materials, e.g., as described in U.S. Pat. Nos. 7,189,233; 7,196,146; 7,309,849; 7,381,209; and 7,981,113; the disclosures of which are herein incorporated by reference. In brief, such PTC matrix materials are fabricated of a non-conductive polymer e.g., polypropylene or medical grade silicone polymer, that exhibits two phases that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure through a selected temperature range. The polymer is designed to transition to an at least partly amorphous phase from the crystalline state at a selected temperature range. In the amorphous state, the molecules are aligned more randomly, and there may be slight changes in material geometry at the macroscale. The non-conductive polymer is combined with a dispersed, highly conductive particles (e.g., carbon micro- or nanoparticles) to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance. Examples of such RF devices are further described in PCT application serial no. PCT/US2014/029556, the disclosure of which is herein incorporated by reference.

In certain embodiments, a non-RF ablative surgical device is employed to practice the subject methods. Non-RF ablative surgical devices of interest include, but are not limited to, cryothermy ablative surgical devices, laser ablative surgical devices, microwave ablative surgical devices, ultrasound ablative surgical devices, a cautery, or the like. In some embodiments, the methods can include other methods of ablation, such as surgical incision, e.g., using a bladed device such as a scalpel.

Ablative devices useful for performing pulmonary vein isolation are commercially available and include the Isolator® Multifunctional Pen or Isolator® Synergy™ Cardiac Ablation Clamp (both marketed by AtriCure, Inc., Cincinnati, Ohio), or other similar devices such as the Cardioblate™ Ablation System (Medtronic, Minneapolis, Minn.), the AFx FLEX 10™ microwave ablation probe (Guidant corporation), the Surgifrost™ Cryoablation System (Cryocath Technologies), or the Epicor™ High Intensity Focused Ultrasound Cardiac Ablation system (St Jude Medical, St Paul, Minn.), for example.

As summarized above, the methods of the present disclosure include performing a left atrial appendage modification. The left atrial appendage (LAA) is a cavity having a shape resembling a small finger or windsock and which is connected to the lateral wall of the left atrium between the mitral valve and the root of the left pulmonary vein. The LAA can be a frequent source of thromboemboli in patients with atrial fibrillation.

By "left atrial appendage modification" is meant any structural and/or functional modification of the LAA, including occlusion, obliteration, and/or exclusion (e.g., via amputation/appendectomy) of the LAA, for example.

According to certain embodiments, the left atrial appendage modification includes left atrial appendage occlusion. Any suitable approach for occluding the LAA may be implemented. Occluding the LAA may involve, e.g., ligation, sutures, staples, or implantable devices. The occlusion may include implanting a closure device and/or providing a filling material in the LAA, thereby sealing the opening of the LAA and preventing any blood clots from exiting therefrom. Devices useful for performing left atrial appendage occlusion are commercially available and include, e.g., endoscopic no-knife stapling devices, such as an Ethicon™ EZ 45 NK device (Ethicon Endo-Surgery, Inc., Cincinnati, Ohio), the WATCHMAN® left atrial appendage closure device (AtriTech, Plymouth, Minn.), the Cosgrove-Gillinov Left Atrial Appendage Occlusion System (Atricure, Cincinnati, Ohio), the Cardioblate® Closure™ Left Atrial Appendage Occlusion Device (Medtronic, Minneapolis, Minn.), and the percutaneous left atrial appendage transcatheter occlusion (PLAATO) system.

In certain aspects, the left atrial appendage modification includes left atrial appendage amputation (e.g., left atrial appendectomy). Any suitable approach for amputating the LAA may be employed. In certain aspects, the LAA is amputated using a mechanical cutting device, such as a cutting stapling device (e.g., an Ethicon EZ 45 K device), surgical blade (e.g., a scalpel), lancet, drill bit, rasp, trocar, harmonic scalpel, or a combination thereof. The amputation may entail a complete or partial resection of the LAA. In some embodiments, amputation of the LAA includes occluding or excluding the LAA prior to amputation. For example, the LAA can be occluded utilizing an endoscopic no-knife stapling device, such as an Ethicon™ EZ 45 NK device (Ethicon Endo-Surgery, Inc., Cincinnati, Ohio) or a left atrial appendage clip (LAA) clip (AtriCure Inc., Westchester, Ohio) which is placed at the base of the appendage. Placement can be confirmed by transesophageal echocardiography. In embodiments in which staples are used, an initial row of staples can be placed across the base of the left atrial appendage, and if it is determined that the exclusion is incomplete, one or more additional rows of staples can be placed. After the exclusion is complete, the left atrial appendage can be amputated with a cutting stapling device, such as an Ethicon EZ 45 K device, and the appendage removed. In certain aspects, such an approach is carried out using an integrated endoscopic occlusion amputation device. Examples of devices finding using in left atrial appendage amputation further include those devices described in international application no. PCT/US2014/029556; the disclosure of which is herein incorporated by reference.

In some embodiments, methods of the present disclosure further include dividing the posterior pericardial attachments of the superior left atrium. The posterior superior aspect of the left atrium is in continuity with the visceral surface of the pericardium. These investitures are areas where the intrinsic nervous system of the heart has sympathetic and parasympathetic nervous system input. These areas affect the rate and rhythm of the heart and the intrinsic nervous system of the heart has been implicated in the pathogenesis of atrial fibrillation (AF). Division of these structures as described below has an additive effect to pulmonary vein isolation in correcting atrial fibrillation (AF). Any suitable approach for dividing the posterior pericardial attachments may be used. For example, the attachments may be divided using a scalpel or other surgical blade. According to certain embodiments, the attachments are divided by cauterization, e.g., the burning, scarring, or cutting of tissue by means of heat, cold, electric current, caustic chemicals, or the like. A cautery device may be employed to divide the posterior pericardial attachments. Cautery devices of interest include, but are not limited to, high-temperature cautery devices, low-temperature cautery devices, electrocautery devices, ultrasonic cautery devices, radiofrequency cautery devices, cautery pens, and the like. In certain aspects, the posterior pericardial attachments are divided using a hand-held cautery device (e.g., a cautery pen), such as a high- or low-temperature "Bovie" cautery device manufactured by Bovie Medical Corporation (Melville, N.Y.).

Utility

The subject methods find use in a variety of different applications where, e.g., it is desirable to reduce the risk of postoperative atrial fibrillation (AF) and/or stroke following a cardiac surgical procedure. Approximately 350,000 patients undergo open heart surgical procedures in the United States each year. Of those, 50,000 are "redo" and/or AF patients undergoing an AF ablation procedure. That leaves 300,000 cardiac surgical procedure patients who will not undergo any AF ablation treatment at all. Of those 300,000 patients, approximately 30% (i.e., 90,000) will develop post-operative AF. The cost of treating each postoperative AF patient while at the hospital is about $11,000 in 2013. Accordingly, these post-operative AF patients amount to a total healthcare cost of nearly $1 billion per year in 2013. Combining pulmonary vein isolation and left atrial appendage modification with the cardiac surgical procedure according to the subject methods to "prophylactically" treat non-AF patients would dramatically reduce healthcare costs associated with postoperative AP and/or postoperative stroke, particularly when the reduction in length of stay (LOS) of hospitalization and actual hospital charges to treat POAF and its sequelae are taken into consideration.

Moreover, by including left atrial appendage (LAA) modification, the subject methods are useful for preventing stroke in post-operative cardiac surgical procedure patients. In view of the challenges and limitations of oral anticoagulation, and the prominent role of the LAA in post-operative thromboembolism (which may or may not be AF-related), the methods of the present disclosure find use in stroke prophylaxis in patients (e.g., non-AF patients) undergoing a cardiac surgical procedure. Accordingly, practicing the methods of the present disclosure results in a further reduction in healthcare costs in addition to those described above with respect to post-operative AF prophylaxis.

Kits

Aspects of the present disclosure also include kits. The subject kits may include, e.g., any surgical devices, systems, or tools that find use in practicing the methods of the present disclosure. In certain aspects, kits of the present disclosure include a device configured to perform a pulmonary vein isolation procedure, and a device configured to perform a left atrial appendage modification.

Devices configured to perform a pulmonary vein isolation procedure may be as described above in the description of the subject methods. According to certain embodiments, the device is an ablative device. The ablative device may be an ablative surgical device. In certain aspects, the device configured to perform a pulmonary vein isolation procedure is a radiofrequency ablative surgical device. The radiofrequency ablative surgical device may be a single point radiofrequency ablative surgical device, e.g., a device which transmits RF energy from a single point at the tip of the device. In other aspects, the radiofrequency ablative surgical device is a multielectrode (e.g., "multipolar") radiofrequency ablative surgical device, e.g., a device that transmits RF energy from two or more electrodes (e.g., 2, 3, 4, 5, 6, 7, 8, or more electrodes). In certain aspects, when the subject kits include a multielectrode radiofrequency ablative surgical device, such device may be a bipolar or quadripolar ablative surgical device. The terms "bipolar" and "quadripolar" indicate that the ablation path extends locally between two or four electrodes (respectively) in the device, rather than between one electrode and a general remote, or external electrode. In certain aspects, the ablative device may incorporate the Positive Temperature Coefficient (PTC) material so that during the ablation process, when tissue temperature rises from ablation process, the resistance of tissue increases slowly to provide more uniform ablation to achieve transmural lesions. Such devices may be configured to deliver ablation energy to achieve a uniform, superficial depth of ablation between ~500 µm and ~1,000 µm.

In certain aspects, a non-RF ablative surgical device for perform a pulmonary vein isolation is included in the kits. Non-RF ablative surgical devices of interest include, but are not limited to, cryothermy ablative surgical devices, laser ablative surgical devices, microwave ablative surgical devices, ultrasound ablative surgical devices, a cautery, or the like. In some embodiments, the device for performing the pulmonary vein isolation is a surgical incision device, e.g., a bladed device such as a scalpel.

Ablative devices configured to perform pulmonary vein isolation which may be included in the subject kits are commercially available and include the Isolator® Multifunctional Pen or Isolator®Synergy™ Cardiac Ablation Clamp (both marketed by AtriCure, Inc., Cincinnati, Ohio), or other similar devices such as the Cardioblate™ Ablation System (Medtronic, Minneapolis, Minn.), the AFx FLEX 10™ microwave ablation probe (Guidant corporation), the Surgifrost™ Cryoablation System (Cryocath Technologies), or the Epicor™ High Intensity Focused Ultrasound Cardiac Ablation system (St Jude Medical, St Paul, Minn.), for example.

As summarized above, kits of the present disclosure also include a device configured to perform a left atrial appendage modification. Devices configured to perform a left atrial appendage modification may be as described above in the description of the subject methods. According to certain embodiments, the device configured to perform a left atrial appendage modification is an appendage occlusion device. The occlusion device may be a ligation device, a suturing device, a stapling device, a device capable of filling the LAA with a filling material, or an implantable device, for example. Occlusion devices which may be included in the subject kits include, but are not limited to, commercially available devices, e.g., endoscopic no-knife stapling devices, such as an Ethicon™ EZ 45 NK device (Ethicon Endo-Surgery, Inc., Cincinnati, Ohio), the WATCHMAN® left atrial appendage closure device (AtriTech, Plymouth, Minn.), the Cosgrove-Gillinov Left Atrial Appendage Occlusion System (Atricure, Cincinnati, Ohio), the Cardioblate® Closure™ Left Atrial Appendage Occlusion Device (Medtronic, Minneapolis, Minn.), and the percutaneous left atrial appendage transcatheter occlusion (PLAATO) system.

In certain aspects, the device configured to perform a left atrial appendage modification is an appendage amputation device. In some embodiments, the appendage amputation device is a mechanical cutting device, such as a cutting stapling device (e.g., an Ethicon EZ 45 K device), surgical blade (e.g., a scalpel), lancet, drill bit, rasp, trocar, harmonic scalpel, or a combination thereof. In certain aspects, where it is desirable to occlude the LAA prior to amputation, the kits may include a stapling device (e.g., a no-knife stapling device, such as an Ethicon™ EZ 45 NK device (Ethicon Endo-Surgery, Inc., Cincinnati, Ohio)) or a left atrial appendage clip (LAA) clip (AtriCure Inc., Westchester, Ohio) for occluding the LAA. For amputation following occlusion, the kit may include a cutting device, such as a cutting stapling device (e.g., an Ethicon EZ 45 K device). In certain aspects, kits of the present disclosure may include an integrated device for occlusion and amputation of the LAA, such as an integrated endoscopic occlusion amputation device.

Kits of the present disclosure may include any other useful components. For example, the kits may further include a device configured to divide the posterior pericardial attachments of the superior left atrium. In certain aspects, such a device is a cautery capable of burning, scarring, or cutting the posterior pericardial attachments by means of heat, cold, electric current, caustic chemicals, or the like. Cautery devices of interest include, but are not limited to, high-temperature cautery devices, low-temperature cautery devices, electrocautery devices, ultrasonic cautery devices, radiofrequency cautery devices, cautery pens, and the like. In certain aspects, the posterior pericardial attachments are divided using a hand-held cautery device (e.g., a cautery pen), such as a high- or low-temperature "Bovie" cautery device manufactured by Bovie Medical Corporation (Melville, N.Y.).

In addition to the above-mentioned devices, a subject kit may further include instructions for using the devices of the kit, e.g., to practice the subject method. The instructions for practicing the subject method utilizing the devices included therewith are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. portable flash drive, CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of performing an aneurysm repair procedure on heart tissue of a living subject, the method comprising:
   at least partially electrically isolating one or more pulmonary veins of the living subject; and
   modifying a left atrial appendage of the living subject;
   wherein the living subject is not diagnosed with an atrial fibrillation and has not been diagnosed as having a predisposition to experience postoperative atrial fibrillation.

2. The method according to claim 1, wherein modifying the left atrial appendage comprises left atrial appendage occlusion.

3. The method according to claim 1, wherein modifying the left atrial appendage comprises left atrial appendage amputation.

4. The method according to claim 1, wherein the method reduces the risk of postoperative atrial fibrillation.

5. The method according to claim 1, wherein the method further comprises dividing posterior pericardial attachments of a superior left atrium of the heart of the living subject.

6. The method according to claim 5, wherein the posterial pericardial attachments are divided with a hand-held cautery device.

7. The method according to claim 1, wherein the living subject has not been tested for predisposition to experience postoperative atrial fibrillation.

8. The method according to claim 1, wherein the living subject has been tested for predisposition to experience postoperative atrial fibrillation and has been diagnosed as not having a predisposition to experience postoperative atrial fibrillation.

\* \* \* \* \*